United States Patent [19]

Kobayashi et al.

[11] Patent Number: 4,916,255

[45] Date of Patent: Apr. 10, 1990

[54] METHOD FOR PRODUCTION OF METHACRYLATE ESTER

[75] Inventors: Akihiro Kobayashi; Toshiyuki Fujita; Takayuki Saito, all of Hitachi; Toshio Akima, Ichihara, all of Japan

[73] Assignee: Hitachi, Ltd., Tokyo, Japan

[21] Appl. No.: 194,347

[22] Filed: May 16, 1988

[30] Foreign Application Priority Data

May 19, 1987 [JP] Japan ................................ 62-121548
Oct. 23, 1987 [JP] Japan ................................ 62-268948

[51] Int. Cl.$^4$ ............................................. C07C 67/02
[52] U.S. Cl. ................................... 560/217; 560/220
[58] Field of Search ........................................ 560/217

[56] References Cited

U.S. PATENT DOCUMENTS

| | | | |
|---|---|---|---|
| 2,129,694 | 9/1938 | Izard | 560/217 |
| 2,891,990 | 6/1959 | Mulvany | 560/217 |
| 3,607,912 | 9/1971 | Russell | 560/217 |
| 4,458,088 | 7/1984 | Hardman | 560/217 |

*Primary Examiner*—Paul J. Killos
*Attorney, Agent, or Firm*—Antonelli, Terry & Wands

[57] ABSTRACT

Methacrylate esters of alcohols having an ether linkage and/or an alicyclic ring can be obtained with no trouble of coloration or polymer formation during the production and for the product. An alcohol having an ether linkage and/or an alicyclic ring is treated with an alkaline substance, and the treated alcohol is caused to react with methyl methacrylate for a transesterification reaction in the presence of an alkaline substance.

32 Claims, No Drawings

METHOD FOR PRODUCTION OF METHACRYLATE ESTER

The present invention relates to a method for producing methacrylate esters, particularly, methacrylate esters of alcohols having an ether linkage and/or an alicyclic ring.

Methacrylate esters of alcohols having an ether linkage are easily oxidized because of the either linkage becoming polymerizable during their synthesis and purification, and so they are known as compounds difficult to be prepared. Even when they are synthesized without the polymerization, it is very difficult to prevent such problems as their serious coloration and poor storage stability.

Japanese Patent KOKOKU No. 49449/1977 and Japanese Patent KOKAI No. 50313/1975 disclose methods for obtaining methacrylate esters of alcohols having an ether linkage by neutralizing a reaction solution obtained by esterification reaction with an aqueous alkali solution, separating the oil layer, and distilling the same to obtain the product of slightly colored and storage stable.

Further, Japanese Patent KOKAI No. 106057/1987 teaches a method through which a slightly colored product is obtained when a mixture of methacrylic acid, a polyether polyol and an acidic catalyst is heated, and a phenolic polymerization inhibitor is added to the mixture at 70° C.

In these references, however, descriptions about methods for preventing the polymerization during synthesis are those for the production of general methacrylate esters, and these methods often fail in preventing the polymerization.

In Japanese Patent KOKOKU No. 49449/1977 and Japanese Patent KOKAI No. 50313/1975, methacrylate esters are tought to be puirfiabled by distillation, however, they are apt to be polymerized under heating and those purifiable by distillation are limited to only a few methacrylate esters. Therefore, these methods cannot be employed for the improvement in coloration and storage stability of methacrylate esters having an ether linkage at large.

The method disclosed in Japanese Patent KOKAI No. 106057/1987 prevents the polymerization only insufficiently and is effective unsatisfactorily for obtaining a light-colored product.

In the production of methacrylate esters of alicyclic alcohols, the alicyclic alcohol is easily oxidized to its peroxide to result in polymerization of the raw material methyl methacrylate and the product ester. Therefore, it is difficult to prevent the polymerization during the reaction by means of conventional methods.

As a method for preventing polymerization during the production of a methacrylate or acrylate ester of an alicyclic alcohol, Japanese Patent KOKAI No. 213733/1983 mentions a method comprising adding an organic sulfonic acid to an alicyclic alcohol, heat-treating the resulting mixture, adding thereto methacrylic acid or acrylic acid, and then causing the esterification reaction.

Particularly in the esterification with alicyclic alcohols having a tertiary carbon atom or a double bond, serious coloration tends to occur. As a method for removing coloring substances formed during the reactions, there is disclosed in Japanese Patent KOKAI No. 138142/1981, which comprises reacting the alcohol in the presence of an acid catalyst, adding an aliphatic hydrocarbon solvent to precipitate the coloring substances, and removing the precipitate therefrom.

However, the method using a strong acid as the catalyst as disclosed in Japanese Patent KOKAI No. 213733/1983 is disadvantageous in that there occurs a side reaction in which the alicyclic structure moiety is polymerized in a manner of ionic reaction and that serious coloration is caused during the reaction owing to the coloring properties of the catalyst itself. These tendencies are remarkable particularly in the case of alicyclic alcohols having a tertiary carbon atom or a double bond. Moreover, there are problems in that in the case of alicyclic secondary or tertiary alcohols, an intramolecular dehydration is caused to result in the decomposition of alcohol. Therefore, the acid is restricted to organic sulfonic acids in the above reference, but the occurrence of intramolecular dehydration cannot be prevented.

The method for removing coloring components as disclosed in Japanese Patent KOKOKU No. 138142/1981 is disadvantageous in that it requires an aliphatic hydrocarbon solvent of more than several times as much as the desired ester compound to result in a low productivity.

As described above, a method comprising esterifying an alicyclic alcohol with methacrylic acid in the presence of an acid catalyst is disadvantageous from the viewpoint of the purity and coloration of the resulting reaction solution.

There has not been known about a method for obtaining a methacrylate of an alicyclic alcohol ester by a transesterification reaction of an alicyclic alcohol with methyl methacrylate, in which the polymerization is suprressed. In general, synthesis of a methacrylate ester by a transesterification reaction is carried out in the presence of a polymerization inhibitor, however, it is usually difficult to prevent the polymerization in the synthesis of a methacrylate ester of an alicyclic alcohol by means of a polymerization inhibitor used in transesterification reactions.

Accordingly, it is an object of the present invention to provide a method for producing methacrylate esters of an alcohols having an ether linkage and/or an alicyclic ring by the transesterification reaction in which the polymerization during synthesis and purification processes are prevented to give methacrylate esters of only slightly colored and excellent in the storage stability.

That is to say, the present invention relates to a method for producing methacrylate esters of alcohols having an ether linkage and/or an alicyclic ring which comprises treating said alcohol with an alkaline substance, and then subjecting the treated alcohol to a transesterification reaction with methyl methacrylate in the presence of an alkaline substance.

In this invention, an alcohol having an ether linkage is an alcohol having a polyalkylene glycol type ether linkage in the molecule, and such compounds as ring opening polymerization products of an alkylene oxide including ethylene oxide, propylene oxide or the like, or compounds formed by addition of an alkylene oxide to an alcohol, phenol or the like are included.

As to the alcohols having an ether linkage, preferably used compounds are represented by the following general formula (I), (II) or (III):

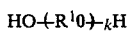         (I)

wherein R¹ is an alkylene group, and k is an integer,

wherein R¹ is an alkylene group, R² is a hydrocarbon group, and l is an integer, or

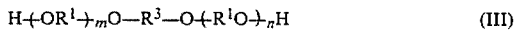

wherein R¹ is an alkylene group, R³ is a divalent hydrocarbon group, and each of m and n is an integer.

As the compounds of the above general formula (I), preferable ones are compounds in which R¹ is an alkylene group having 2 to 5 carbon atoms and k is an integer of 2 to 30.

The compounds of the above general formula (I) include diethylene glycol, triethylene glycol, tetraethylene glycol, polyethylene glycol, dipropylene glycol, tripropylene glycol, tetrapropylene glycol and polypropylene glycol.

As the compounds of the above general formula (II), preferable ones are compounds in which R¹ is an alkylene group having 2 to 5 carbon atoms, R² is a saturated or unsaturated aliphatic hydrocarbon group having 20 or less carbon atoms, a saturated or unsaturated alicyclic hydrocarbon group having 20 or less carbon atoms, or an aromatic hydrocarbon group having 20 or less carbon atoms, and l is an integer of 1 to 30.

The compounds of the above general formula (II) include compounds formed by addition of ethylene oxide, propylene oxide or the like to such a monohydric alcohol as methanol, ethanol, propanol, allyl, alcohol, butanol, pentanol, cyclopentanol, hexanol, cyclohexanol, norborneol, norbornenyl alcohol, norbornylmethyl alcohol, norbornenylmethyl alcohol, adamantanol, tricyclo[5.2.1.0$^{2,6}$]deca-3-en-8-ol, tricyclo[5.2.1.0$^{2,6}$]deca-3-en-9-ol, tricyclo[5.2.1.0$^{2,6}$]decan-8-ol, tricyclo[5.2.1.0$^{2,6}$]decan-3-ylmethanol, tricyclo[5.2.1.0$^{2,6}$]decan-4-ylmethanol, borneol, isoborneol or a monohydric phenol such phenol and alkylphenol; and compounds formed by addition of ethylene glycol, propylene glycol or the like to tricyclo[5.2.1.0$^{2,6}$]-deca-3,8-diene (common name: dicyclopentadiene) followed by addition-polymerization to the resulting adduct of ethylene oxide, propylene oxide or the like.

As the compounds of the above general formula (III), preferable ones are compounds in which R¹ is an alkylene group having 2 to 5 carbon atoms, R³ is a saturated or unsaturated divalent hydrocarbon group having 20 or less carbon atoms, a saturated or unsaturated divalent alicyclic hydrocarbon group having 20 or less carbon atoms, or a divalent group with an aromatic hydrocarbon group having 20 or less carbon atoms which may have the structural unit of —O— or —SO$_2$—, and each of m and n is an integer, the sum of m and n being 2 to 30.

The compounds of the above general formula (III) include compounds formed by addition-polymerization of ethylene oxide, propylene oxide or the like to a polyhydric alcohol such as 1,4-butanediol, 1,3-butanediol, 1,6-hexanediol, cyclohexanedimethylol, 3,8-bis(hydroxymethyl)tricyclo[5.2.1.0$^{2,6}$]decane, 3,9-bis(hydroxymethyl)tricyclo[5.2.1.0$^{2,6}$]decane and 4,8-bis(hydroxymethyl)tricyclo[5.2.1.0$^{2,6}$]decane, and to a polyhydric phenol such as bisphenol A, bisphenol S, and bis(p-hydroxyphenyl) ether.

Among alcohols having an ether linkage, those having a double bond or an alicyclic structure in the molecule are particularly easily oxidizable. Such either linkage having alcohols are considered to be in an oxidized state when they are allowed to stand in the air and the oxidization proceeds when air is blown through the alcohol. When an ether linkage having alcohol in such an oxidized state is reacted with methyl methacrylate, there is caused polymerization due to the methacryloyl double bond during the synthesis and purification resulting in such adverse effect as the coloration of product with poor storage stability.

The undesirable polymerization reaction and coloration has been suppressed according to the present invention by treating the oxidized ether linkage having alcohol with an alkaline substance to decompose the oxidized substances.

The present invention further relates to a method for producing methacrylate esters of an alicyclic alcohol having or not having an ether linkage.

In the invention, the alicyclic alcohol is an alcohol having an alicyclic group in the molecule, and it includes bicyclo[2.2.1]hept-2-en-5-ol, bicyclo[2.2.1]heptan-2-ol, cyclohexanemonomethylol, cyclohexanedimethylol, bicyclo[2.2.1]hept-2-en-5-ylmethanol, bicyclo[2.2.1]heptan-2-ylmethanol, 1-adamantanol, 2-adamantanol, tricyclo[5.2.1.0$^{2,6}$]deca-3-en-8(or 9)-ol, tricyclo[5.2.1.0$^{2,6}$]decan-8-ol, tricyclo[5.2.1.0$^{2,6}$]decan-3-(or 4)-ylmethanol, 3(or 4), 8(or 9)-bis(hydroxymethyl)tricyclo[5.2.1.0$^{2,6}$]decane, borneol, isoborneol, fenchyl alcohol, 2,2,5trimethylcyclohexanol, menthol, ethylene glycol monodicyclopentenyl ether, propylene glycol monodicyclopentenyl ether, neopentyl glycol monodicyclopentenyl ether, 1,6-hexanediol monodicyclopentenyl ether or the like.

Among the alicyclic alcohols, those having a tertiary carbon atom or a double bond in the alicyclic group are particularly liable to form a peroxide by air oxidation. In particular, alcohols having both a tertiary carbon atom and a double bond in the alicyclic ring and, for example, alcohols having dicyclopentadiene strucuture

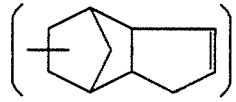

or norbornene strucuture

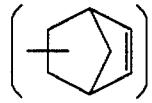

are oxidized by air very easily to give peroxides. Such alicyclic alcohols contain the peroxide as impurities, and the amount of peroxides is increased, when they are allowed to stand in the air and furthermore increased when air is blown through them.

The undesirable polymerization reaction has been suppressed according to the present invention by subjecting the alcohol to catalytic treatment with an alkaline substance to decompose the perioxide.

The alkaline substance includes sodium, potassium, lithium, magnesium, calcium, sodium hydride, potassium hydride, lithium hydride, butyl lithium, phenyl lithium, sodium hydroxide, potassium hydroxide, lithium hydroxide, methoxides, ethoxides, propoxides or butoxides of sodium, potassium or lithium, and alkoxides of said alcohols.

The alkaline substance is preferably at least one compound selected from the group consisting of sodium, potassium, lithium, and hydroxides and alkoxides thereof. From the handling viewpoint of low corrosiveness and no hydrogen generation at the time of reaction, hydroxides and alkoxides of sodium, potassium and lithium are more preferable. Lithium hydroxide, lithium methoxide, lithium ethoxide, lithium propoxide and lithium butoxide are the most preferable ones.

These alkaline substances may be used in a form of solution or dispersion in a solvent of, for example, an alcohol such as methanol, ethanol or the like.

The amount of the alkaline substance used for the treatment is preferably 0.01 to 5.0%, particularly preferably 0.05 to 2.0%, by weight based on weight of the starting alcohol. When the amount of alkaline substance is too small, sufficient decomposing effect on the oxide can not be obtained, while this effect is not particularly improved even when the amount is too large.

The entire amount of the alkaline substance may be added to the raw material alcohol at the beginning to be followed by the treatment and reaction, or the amount of alkaline substance may be added divisionally during the treatment or the transesterification reaction.

The starting alcohol is treated with the alkaline substance preferably in a reactor equipped with a conventional stirrer. It is also possible to place the alkaline substance in a storage vessel containing the starting alcohol, however, since many of the alkaline substances are solid and are not easily soluble in the alcohol, the treatment is more efficiently conducted when the treatment liquid is allowed to flow to some extent by stirring or the like.

Although the treatment conditions vary depending on the kind and amount of alkaline substance used, the treatment is carried out preferably at a temperature of 0° to 120° C. Although the treatment time may be determined properly, a sufficient treatment time is 5 hours or less. For example, when a metallic alkali is used, the treatment temperature is preferably low and the treatment can be finished at a low temperature in a substantially short time. On the other hand, when there is used an alkaline substance which is difficulty soluble in the raw-material alcohol such as an alkali hydroxide, the solid and liquid contact is carried out preferably with heating or treating for a long period of time in some cases. Anyway, the purpose can usually be achieved by gentle stirring for 1 minute to 1 hour at room temperature without particular heating or cooling. In practical production facilities, when the alkaline substance is added to the starting alcohol and followed by adding thereto methyl methacrylate, it takes a certain period of time to charge methyl methacrylate. Therefore, said treatment can be substantially achieved even when methyl methacrylate is charged immediately after the addition of the alkaline substance to the starting alcohol to carry out the ester exchange reaction described hereinafter. Unless the alkaline substance is removed from the starting alcohol after the treatment, formation of an oxide in the treated alcohol can be suppressed even when it is stored for several days. Therefore, said stored treated liquor can be subjected to the ester exchange reaction with methyl methacrylate.

Since said alkaline substance functions as a catalyst for the transesterification reaction, it is possible to add methyl methacrylate to said treated liquor to carry out the transesterification reaction without removing the alkaline substance from said treated liquor after said treatment. If necessary, the alkaline substance can be removed from the treated liquor by neutralization with an acid, washing with water or filtration.

In the transesterification reaction of the starting alcohol with methyl methacrylate, the alkaline substance is present in an amount of preferably 0.01 to 10.0%, particularly preferably 0.05 to 5.0%, by weight based on the weight of the starting alcohol. When the amount of the alkaline substance is too small, the rate of transesterification reaction is slowed down. Too large an amount of the alkaline substance has no particular advantage and results in a troublesome procedure for removing the alkaline substance after completion of the reaction.

When the alkaline substance is not separated from said treatment liquid, the alkaline substance needs not to be freshly added at the time of the ester exchange reaction, or may be added properly so as to be present in the above amount thereof for the ester exchange reaction.

As the alkaline substance present at the time of the transesterification reaction, those described above can be used, and this alkaline substance has a function of suppressing formation of an oxide during the transesterification reaction.

In the transesterification reaction, methyl methacrylate is used preferably in an amount of 2 to 10 moles per equivalent of the hydroxide group of the starting alcohol. When the amount of methyl methacrylate is too small, the reaction rate is slowed down, so that the unreacted alcohol tends to remain. On the other hand when the amount of methyl methacrylate is too large, the productivity is lowered and moreover a long period of time is required for a step of recovering the surplus methyl methacrylate after completion of the reaction.

In the present invention, the presence of a polymerization inhibitor at the time of the transesterification reaction is preferred. As the polymerization inhibitor, there can be used conventional ones such as hydroquinone, hydroquinone monomethyl ether, t-butyl-catechol, parabenzoquinone, 2,5-diphenylparabenzoquinone, phenothiazine, diphenylamine, phenyl-$\beta$-naphthylamine and methylene blue. The amount of polymerization inhibitor is preferably 15 to 10,000 ppm, particularly preferably 50 to 1,000 ppm, relative to the starting alcohol. When the amount is too small, the polymerization inhibiting effect becomes insufficient in some cases. When the amount is too large, adverse effects are brought about in some cases. For example, when a product from which the polymerization inhibitor has not been removed is subjected to polymerization, the polymerization inhibitor inhibits the polymerization. Hydroquinone monomethyl ether and phenothiazine are particularly preferred because when they are used, only slightly colored reaction mixture is obtained. In the present invention, it is preferable to blow a small amount of molecular oxygen through the reaction mixture during the reaction in order to prevent the reaction mixture from undergoind polymerization. Molecular oxygen is used in a diluted form as in the form of air. When a fractionating column is used as described hereafter, passing of molecular oxygen through the reaction mixture is also preferable for preventing polymerization of methyl methacrylate present as gas or liquid in said column. Although the amount of molecular oxygen differs depending on shape of the reactor and stirring conditions, molecular oxygen is blown into the reaction mixture at a rate of 5 to 500 ml/min (25 to 2,500 ml/min in terms of air) per mole of the starting alcohol charged.

The transesterification reaction is carried out preferably at 60° to 130° C. at atmospheric pressure or under pressure.

As to the mode of the transesterification reaction, there can be employed a method generally known to those skilled in the art in which a methacrylate ester is produced by the transesterification reaction of methyl methacrylate with an alcohol. In this method, the reaction is carried out preferably while removing secondarily formed methanol from the system by the azeotropic distillation of methanol and methyl methacrylate in order to improve the conversion of the starting alcohol.

Therefore, as the reactor, a batch-type reactor equipped with a fractionating column is preferred. In this case, the transesterification reaction is carried out, for example, in the following manner. When the reaction is carried out at atmospheric pressure, methanol and methyl methacrylate formed boil when the temperature of reaction mixture rises to about 100° C. In the fractionating column, the amount of methyl methacrylate distilled off from the system is reduced as much as possible by controlling the reflux ratio to be at about 1 to 20 range so as to make the temperature at the top of column is maintained at 64°–70° C. of the azeotropic temperature of methanol and methyl methacrylate.

While the methanol is being removed from the system as an azeotrope with methyl methacrylate, the transesterification reaction is completed. In this case near the end of the reaction, the temperature of the reaction mixture rises to about 110° to 125° C. and the temperature at the column top becomes about 100° C. Therefore, the composition at the column top becomes to be deviated from the azeotropic composition of methanol and methyl methacrylate so that it is preferable to increase the reflux ratio to 10 or more in order to reduce the loss of methyl methacrylate.

On the other hand, when methanol is reserved in the reaction system at a high concentration for a long period of time, a by-product is formed by addition of methanol to the unsaturated bond of methacylate ester. Therefore, it is also necessary to remove the formed methanol by distillation as soon as possible in order to reduce the by-product.

A large amount of liquid and gas of methyl methacrylate remains in the fractionating column because of evaporation thereof from the reactor. However, even when a polymerization inhibitor is charged into the reactor, it is not easily to be evaporated, and hence the polymerization inhibitior does substantially not present in the fractionating column so that there is a fear of polymerization of methyl methacrylate. Therefore, it is preferable to introduce, as described above, molecular oxygen, for example, air into the reactor to allow the oxygen to exist in the fractionating column, or to add a polymerization inhibitor to a reflux solution to be returned from the top of the column to its lower part.

The reaction mixture obtained by the transesterification reaction is often composed of a solution containing methyl methacrylate, the product methacrylate ester, a small amount of the starting alcohol, a polymerization inhibitor, and insoluble materials such as the alkaline substance.

In order to obtain the product methacrylate ester by substantial isolation from this reaction mixture, there can be employed a method widely used in the art. That is to say, methyl methacrylate is removed as it is from the reaction mixture by distillation, and subsequently the desired product methacrylte ester is obtained by distillation usually under pressure. It is also possible to obtain the product by distilling off methyl methacrylate after removing the alkaline substance (a catalyst) and the like by filtering the reaction mixture or by washing it with water, and, if necessary, the product may be further purified by distillation. Furthermore, it is also possible to obtain the product by removing the alkaline substance (a catalyst) and the like by filtration or washing with water removing the methyl methacrylate thereafter from the reaction mixture by distillation. Also in this case, the product may be further purified by distillation. Employment of an alkaline substance such as lithium hydroxide or lithium methoxide is convenient because removal thereof by filtration is easy.

A preferred embodiment of the present invention is described below:

A reactor equipped with a fractionating column (the net number of trays 2 to 5; 2 to 15 trays are sufficient though the number may be larger) is purged with nitrogen. First, the starting alcohol is charged into the reactor. Then, alkaline substance is added and they are stirred. Subsequently, a polymerization inhibitor is added and methyl methacrylate is charged into the reactor. The temperature is raised under stirring at atmospheric pressure or under reduced pressure, and when the temperature of the reaction mixture becomes 50° C., air or oxygen is blown through the reaction mixture. In this case, the air or oxygen to be blown therethrough is preferably dried one which has a water content of 1% by weight or less and more preferably 1,000 ppm or less. Water contained in compressed air can be removed by adsorption with sulfuric acid, molecular sieves, calcium chloride, silica gel or the like or by condensation by cooling. It is also possible to use liquified and purified oxygen as it is or after dilution with nitrogen or the like.

Since the alkaline substance, in some cases, loses it function as catalyst during the reaction owing to the influence of water or moisture in air, it is also effective to add the alkaline substance during the reaction continuously in small portions, or to add the alkaline substance during the reaction additionally every 10 to 30 minutes so as to adjust its total amount required.

When the temperature of the reaction mixture rises to about 100° C. in the case of atmospheric pressure and the vapor begins to generate, the fractionating column is regulated to the total reflux conditions. After the temperature at the top of the column becomes the azeotropic temperature of methanol and methyl methacrylate (64° to 66° C. in case of atmospheric pressure), the reflux ratio is set at 1 to 10 and the secondarily produced methanol is taken out together with its azeotropic partner, methyl methacrylate. The reflux ratio during the reaction is as described above.

As a method for adding a polymerization inhibitor to the reflux to be returned into the fractionating column, there is preferably employed a method comprising dissolving previously in methyl methacrylate the same polymerization inhibitor as contained in the reaction mixture, and adding the resulting solution to the reflux continuously by means of a pump or the like.

For filtering the reaction mixture obtained after completion of the reaction, the reaction mixture is advantageously incorporated with a filter aid (usualy diatomaceous earth, etc.) in an amount of about 0.1 to 2.0% by weight based on the weight of reaction mixture, or to precoat the same on the surface of a filter.

Ether linkage having alcohols are easily oxidized and are often in an oxidized state at the time of use, and they are further oxidized when allowed to stand in the air, and it seems that the amount of the alcohol oxidized is increased greatly when molecular oxygen is blown through the alcohol.

The oxidized matter can be decomposed by treating the alcohol with an alkaline substance. The alcohol is not oxidized and no peroxide is formed in the system under a temperature condition for the transesterification reaction, when air is blown through the reaction mixture in the presence of an alkaline substance and a polymerization inhibitor.

According to the present invention, the polymerization during synthesis and purification is inhibited and it becomes possible to produce an ether linkage having methacrylate ester with light color and excellent storage stability.

The inventors further investigated the behavior of alicyclic alcohols and have found the following facts.

The alicyclic alcohols contain peroxides as impurities, and when they are allowed to stand in the air, amount of the peroxides is increased. And when molecular oxygen (or air) is blown through the alicyclic alcohol, the amount of peroxides is further increased. However, a catalytic treatment of the alcohol with an alkaline substance results in decomposition of the peroxides, and no peroxide is formed under a temperature condition for the transesterification reaction, when air is blown through the reaction mixture in the presence of an alkaline substance and a polymerization inhibitor. Such effects differs remarkably from those obtained by methods explained below.

An alicyclic alcohol containing no peroxide is prepared by its treatment with an alkaline substance and then the alkaline substance is removed. A transesterification reaction is carried out using a neutral catalyst such as titanium tetraisopropoxide, titanium tetrabutoxide or the like. When air is blown through the reaction system, immediate formation of the peroxide followed by polymerization occurs even in the presence of a polymerization inhibitor.

In the case of a method in which an alicyclic alcohol and a polymerization inhibiitor are previously charged and an alkaline catalyst is added immediately before the initiation of the reaction, a considerable amount of a peroxide has been formed and it causes formation of a polymer during the reaction and a small amount of polymer formed before the reaction.

When such an alicyclic alcohol is subjected to the transesterification reaction with methyl methacrylate be use of an acid catalyst such as p-toluenesulfonic acid, sulfuric acid or the like, a side reaction occurs to yield a byproduct by intramolecular dehydration of the alicyclic alcohol. Moreover, the alicyclic alcohol causes ionic polymerization due to the acid catalyst to give oligomeric byproducts and cause serious coloration.

According to the present invention, the side reactions can effectively be suppressed, whereby an only slightly colored methacrylate ester of an alicyclic alcohol can be produced.

The present invention is further explained hereunder in more detail with reference to Examples, which are not be way of limitation but by way of illustration.

In Examples, the judgement on whether a polymer was formed or not and the measurement of peroxide content were conducted in the following manners.

(Judgement on polymer formation)

The judgement was conducted by a methanol solubility test. That is to say, 5 g of the sample and 15 g of methanol were placed in a test tube and mixed by sufficient shaking, and the existence of insoluble materials (appearance of white turbidity) was observed with the nacked eye, whereby the existence of a polymer was judged.

(Measurement of peroxide content)

In a 250-ml Erlenmeyer flask with ground stopper were placed 100 ml of methyl alcohol, 5 ml of a 10% potassium thiocyanate solution and 2ml of 1:1 sulfuric acid. Then, 10 ml of a 1/10N ferrous ammonium sulfate solution was added by means of a pipette. A small piece of solid carbon dioxide was added and the air in the flask was replaced with carbon dioxide gas, and the greased stopper was put in the flask and the flask was allowed to stand for 15 minutes. A 1/50N titanous chloride solution was carefully added until the pink color of ferric iron disappeared. A small piece of solid carbon dioxide was placed in the Erlenmeyer flask to make the atmosphere in the flask inert, and 25 ml of the sample was added by means of a pipette.

After sufficient mixing, the greased stopper was put in the flask and the flask was allowed to stand in the dark. The solution obtained in the flask was carefully titrated with a 1/50N titanous chloride solution until its pink color disappeared. Near the end point of the titration, the titanous chloride solution was added drop by drop and the reaction with titanous chloride was sufficiently carried out.

The peroxide content c (% by weight in terms of hydrogen peroxide) was calculated using the equation:

$$c = \frac{A \times F \times 100}{25 \times G}$$

wherein
 A: amount (ml) of the 1/50N titanous chloride solution required for reducing ferric iron generated by the peroxide in the sample.
 F: titer of the 1/50N titanous chloride solution.
 G: specific gravity of the sample.

The term "1:1 sulfuric acid" means a mixture of water and concentrated sulfuric acid in the ratio of 1:1 by volume. The titer of the 1/50N titanous chloride solution was determined in the following manner: In a 250-ml Erlenmeyer flask with ground stopper were placed 50 ml of distilled water, 15 ml of hydrochloric acid and 10 ml of a 10% potassium thiocyanate solution, and 10 ml of a standard iron solution was added by means of a pipetter. A small piece os solid carbon dioxide was added and the atmosphere in the flask was made inert with carbon dioxide gas. The solution obtained in the flask was titrated with the 1/50N titanous chloride solution until its pink color disappeared, and the titer of the titanous chloride solution was calculated using the equation:

$$F = \frac{0.05 \times 17.01}{A \times 55.85}$$

wherein

A: amount (ml) of, the 1/50N titanous chloride solution required for reducing 10 ml of the standard iron solution.

The standard iron solution was prepared by dissolving 35.11 g of ferrous ammonium sulfate (Mohr's salt) [FeSO$_4$(NH$_4$)$_2$SO$_4$·6H$_2$O] in 400 ml of distilled water, adding 25 ml of concentrated sulfuric acid, heating the resulting solution at 50° to 60° C., adding a potassium permanganate solution until the ferrous ions were oxidized to ferric ions, and then making up the solution thus obtained to 1000 ml with distilled water. The standard iron solution contained 0.005 g of ferrous ions per ml.

EXAMPLE 1

Into a 1-liter four-necked flask equipped with a stirrer, a thermometer, an air inlet tube, and a rectifying column (10 trays; Synder's type) was charged 206 g (0.5 mole) of polyethylene glycol monodicyclopentenyl ether

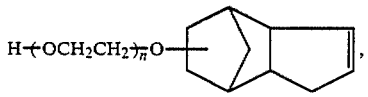

average n value: 6, average molecular weight: 412; obtained by adding ethylene glycol to tricyclo[5.2.1.0$^{2,6}$]deca-3,8-diene in the presence of an acid catalyst followed by additionpolymerization of ethylene oxide). Thereto was added 1.0 g (0.5% by weight based on the weight on the alcohol) of granular lithium hydroxide, followed by gentle stirring at 40° C. for 30 minutes. In the solution thus obtained, lithium hydroxide was in a dispersed state. Then, 200 g (2.0 moles) of methyl methacrylate and 0.12 g of hydroquinone monomethyl ether were charged into the flask, and the temperature was raised while introducing air (water content: 150 ppm) into the reaction mixture at a rate of 50 ml/min. When the temperature of the reaction mixture reached about 100° C., an azeotropic mixture of methanol and methyl methacrylate began to be distilled out from the top of the rectifying column. The reflux ratio was adjusted to about 2 to make the temperature at the top of the column to 64°-66° C., and the reaction was carried out while distilling off the methanol as an azeotrope with methyl methacrylate. Thirty minutes and 1 hour after "the beginning of distilling-out of the azeotropic mixture of methanol and methyl methacrylate" (hereinafter referred to as "the beginning of reaction"), another 0.5 g each of granular lithium hydroxide was added (the total amount of granular lithium hydroxide added including pretreatment was 1.0% by weight based on the weight of the alcohol).

The reaction was continued for 3 hours after the beginning of reaction. The temperature at the top of the column rose to about 90° C. With the temperature rise, the reflux ratio was gradually increased finally to 10, and the reaction was continued for another 1 hour. The reaction mixture at that time, namely 4 hours after the beginning of reaction, was analyzed by a gas chromatography to find that the total amount of polyethylene glycol monodicyclopentenyl ether was 0.5% (by area) based on the total amount of the product methacrylate ester of the alcohol. The reaction was terminated at that point. No polymer formed was contained in the reaction mixture neither during the reaction nor after the termination of the reaction.

Subsequently, the temperature of the reaction mixture was adjusted to 100° C. and a portion of the methyl methacrylate was removed by distillation while reducing the pressure gradually. Finally the pressure was adjusted to 40 mmHg, and the removal of the surplus methyl methacrylate was stopped at the time when the methyl methacrylate content became 0.3% as measured by gas-chromatographic analysis. Then, the reaction mixture was filtered through filter paper (filtration area: 70 cm$^2$, TOYO Roshi K. K.; 5B) at 70° C. with filtration pressure of 1 kg/cm$^2$ (filtration time 13 minutes) to obtain 230 g of light-yellow and transparent liquid (hue: 150 hazen unit). The liquid was analyzed by a gas chromatography to find that purity of the methacrylate ester of the polyethylene glycol monodicyclopentenyl ether was 98.3% (by area). No polymer was detected.

Comparative Example 1

Into the same apparatus as in Example 1 were charged 206 g (0.5 mole) of a polyethylene glycol monodicyclopentenyl ether (the same as in Example 1), 4.0 g of titanium tetraisopropoxide, 0.12 g of hydroquinone monomethyl ether and 200 g (2.0 moles) of methyl methacrylate, and the reaction was carried out while introducing air at a rate of 50 ml/min.

Immediately after the beginning of reaction, the formation of polymer was detected (a small amount of the reaction mixture was collected, and after removing therefrom the titanium tetraisopropoxide, the residue was subjected to the methanol solubility test). When heating was still continued, marked formation of a polymer was observed after about 1 hour, and the reaction solution increased in viscosity to become unable to be stirred.

Comparative Example 2

A polyethylene glycol monodicyclopentenyl ether (the same as in Example 1) was stirred together with lithium hydroxide in the same manner as in Example 1, and then the lithium hydroxide was removed by filtration and the residue was washed with water and then dried over Glauber's salt. Into the same apparatus as in Example 1 were charged 206 g of the polyethyleneglycol monodicyclopentenyl ether treated with the alkaline substance and freed therefrom thereafter, 4.0 g of titanium tetraisopropoxide, 0.12 g of hydroquinone monomethyl ether and 200 g (2.0 moles) of methyl methacrylate. The reaction was carried out in the same manner as in Example 1 while introducing air at a rate of 50 ml/min. Formation of a polymer was detected 1 hour after the beginning of reaction. When heating was still continued, the reaction mixture increased in viscosity to become unable to be stirred after about 1 hour.

Compartive Example 3

Into a 1-liter four-necked flask equipped with a stirrer, a thermometer, an air inlet tube and a reflux condenser with water separator were charged 206 g (0.5 mole) of a polyethylene glycol monodicyclopentenyl ether (the same as in Example 1), 52 g (0.6 mole) of methacrylic acid, 200 g of toluene, 20 g of p-toluenesulfonic acid and 0.12 g of hydroquinone monomethyl ether. The temperature was raised while introducing air at a rate of 50 ml/min, and the reaction mixture was refluxed under heating (100° to 120° C.) while removing the water formed. Immediately after the beginning of reaction, formation of a polymer was detected. When heating was still continued, the reaction solution increased in viscosity to become unable to be stirred, after about 2 hours.

Comparative Example 4

In the same apparatus as in Example 1 were charged 206 g (0.5 mole) of a polyethylene glycol monodicyclopentenyl ether (the same as in Example 1), 0.12 g of hydroquinone monomethyl ether and 200 g (2.0 moles) of methyl methacrylate, and the temperature was raised while introducing air at a rate of 50 ml/min. After 15 minutes, the temperature of the solution in the apparatus rose to 100° C. and methyl methacrylate began to be refluxed. The solution was maintained at 100° C. for 30 minutes, after which 1.0 g of lithium hydroxide was added and the reaction was carried out. At that time, the polymer had already been formed in the reaction mixture. But, since the reaction mixture did not increase in viscosity any more, the reaction was continued and 0.5 g each of lithium hydroxide was added during the reaction when 30 minutes and 1 hour were passed after the beginning of reaction. After 4 hours of reaction, a portion of the methyl methacrylate was distilled off followed by filtration in the same manner as in Example 1. The liquid thus obtained contained a polymer and had brown color (600 hazen unit), and hence was not usable as it was as the product.

Comparative Example 5

Into the same apparatus as in Example 1 were charged 206 g (0.5 mole) of a polyethylene glycol monodicyclopentenyl ether (the same as in Example 1) and lithium hydroxide in an amount of 0.01 g (0.005% based on the amount of the alcohol), and they were stirred at 40° C. for 1 hour. Then, 200 g (2.0 moles) of methyl methacrylate and 0.12 g of hydroquinone monomethyl ether were charged, and the temperature was raised while blowing air (water content: 150 ppm) through the reaction mixture at a rate of 50 ml/min. When no lithium hydroxide was added during the reaction, the reaction stopped at a conversion of 40% after 1 hour from the beginning of reaction. When heating was continued for another 1 hour, the polymer was formed.

EXAMPLE 2

Into the same apparatus as in Example 1 were charged 206 g (0.5 mole) of a polyethylene glycol monodicyclopentenyl ether (the same as in Example 1) and lithium hydroxide in an amount of 16 g (7.8% by weight based on the weight of the alcohol), and they were stirred at 40° C. for 1 hour. Then, 200 g (2.0 moles) of methyl methacrylate and 0.12 g of hydroquinone monomethyl ether were charged, and the temperature was raised to carry out the reaction while the blowing air (water content: 150 ppm) through the reaction mixture at a rate of 50 ml/min. Thirty minutes and 1 hour after the beginning of reaction, another 10 g each of lithium hydroxide was added (the total amount of lithium hydroxide added including the pretreatment: 17.5% by weight based on the weight of the alcohol). In the same manner as in Example 1, a portion of the methyl methacrylate was distilled off followed by filtration. The time required for the filtration was 54 minutes and the amount of the methacrylate ester (hue: 150 hazen unit) obtained was 180 g.

EXAMPLE 3

Into the same apparatus as in Example 1 was charged 206 g (0.5 mole) of a polyethylene glycol dicyclopentenyl ether (the same as in Example 1), followed by adding thereto a 20% methanolic solution of sodium methoxide in an amount of 1.0 g (0.14% by weight, in terms of sodium methoxide, based on the weight of the alcohol), and they were stirred at 25° C. for 30 minutes.

Into the apparatus were charged 200 g (2.0 moles) of methyl methacrylate and 0.12 g of hydroquinone monomethyl ether, and the temperature was raised to carry out the reaction in the same manner as in Example 1, while introducing air (water content: 150 ppm) into the reaction mixture at a rate of 50 ml/min. Between 15 minutes and 3 hours after the beginning of reaction, another 0.5 g each of a 28% methanolic solution of sodium methoxide was added every 15 minutes in 12 times for 6.0 g in total; the total amount of the solution added including the pretreatment was 7.0 g (0.95% by weight, in terms of sodium methoxide, based on the weight of the alcohol).

After completion of the reaction, in the same manner an in Example 1, a portion of the methyl methacrylate was distilled off and filtration was attempted, but pores of the filter paper were plugged and it was difficult to filter the whole residual reaction mixture. Therefore, the sodium methoxide was removed by washing with water amd then the residue was dried over Glauber's salt. Consequently, there was obtained 195 g of a product having a hue of 160 hazen unit and such a purity that the total amount of methacrylate ester of the polyethylene glycol monodicyclopentenyl ether was 98.1% (by area). No polymer was detected.

EXAMPLE 4

Methacrylate ester of a polyethylene glycol monodicyclopentenyl ether was synthesized by carrying out the pretreatment and reaction in exactly the same manner as in Example 1, except that air introduced during the reaction was undried air having a water content of 2.8% by weight. The reaction mixture obtained 4 hours after the beginning of reaction was analyzed by a gas chromatography to find that the total amount of the polyethyleneglycol monodicyclopentenyl ether was 2.4% (by area) based on the total amount of the product methacrylate ester of the alcohol. After completion of the reaciton, a portion of the methyl methacrylate was distilled off, followed by filtration, in the same manner as in Example 1. The time required for the filtration was 37 minutes, and there was obtained 210 g of light-yellow and transparent (hue: 140 hazen unit) liquid containing no polymer. The liquid was analyzed by a gas chromatography to find that it had such a purity that the total amount of methacrylate ester of the polyethylene glycol monodicyclopentenyl ether was 96.2% (by area).

EXAMPLE 5

Into the same apparatus as in Example 1 was charged 291 g (0.4 moles) of a polypropylene glycol monodicyclopentenyl ether

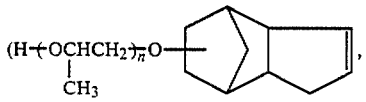

average n value: 10, average molecular weight: 728, obtained by addition to tricyclo[5.2.1.0$^{2,6}$]deca-3-en-8(or 9)-ol and polymerization of propylene oxide), followed by adding thereto 2.0 g of a 10% methanolic solution of lithium methoxide, and they were stirred at 30° C. for 30 minutes. Into the flask were charged 160 g (1.6 moles) of methyl methacrylate and 0.16 g of hydroquinone monomethyl ether, and the reaction was carried out in the same manner as in Example 1. Thirty minutes, 1 hour and 2 hours after the beginning of reaction, another 1.0 g each of a 10% methanolic solution of lithium methoixde was added. After completion of the reaction, no polymer was detected in the reaction mixture. The reaction mixture was filtered by suction through fitler paper (TOYO Roshi K.K.; 5B) on a glass Buchner funnel, and then the methyl methacrylate was removed by distillation under the same conditions as in Example 1 to obtain 305 g of light-yellow and transparent liquid (hue: 200 hazen unit). The liquid contained 98% (saponification value 69 mg KOH/g) of methacrylate ester of the polypropylene glycol monodicyclopentenyl ether. No polymer was contained.

EXAMPLE 6

Into the same apparatus as in Example 1 was charged 146 g (1.0 mole) of an adduct of allyl alcohol with ethylene oxide (CH$_2$=CH—CH$_2$—O (CH$_2$CH$_2$O)$_n$ H, average n value: 2.0, average molecular weight: 146, obtained by addition polymerization of ethylene oxide to allyl alcohol) followed by adding thereto 1.0 g of a 28% methanolic solution of sodium methoxide, and they were stirred at 25° C. for 20 minutes. Into the apparatus were charged 350 g (3.5 moles) of methyl methacrylate and 0.11 g of hydroquinone monomethyl ether, and the reaction was carried out in the same manner as in Example 1. Every 30 minutes after the beginning of reaction, another 0.5 g each od a 28% methanolic solution of sodium methoxide was added. After completion of the reaction (after 4 hours), the reaction mixture contained no polymer formed.

The reaction mixture was washed with water to removed the sodium methoxide, and the methyl methacrylate was distilled off to obtain 210 g (yield 98%) of light-yellow and transparent liquid (hue: 80 hazen unit). By gas-chromatographic analysis, it was found that the methacrylate ester of the adduct of allyl alcohol with ethylene oxide had a purity of 98.7% and contained no polymer.

In a 18 mm$\phi$ test tube was placed 10 g of the methacrylate ester of the adduct of allyl alcohol with ethylene oxide, and heated at 110° C. for 2 hours. But any change such as formation of a polymer was not observed.

Comparative Example 6

Into the same apparatus as in Comparative Example 3 were charged 146 g (1.0 mole) of an adduct of allyl alcohol with ethylene oxide (the same as in Example 3), 103 g (1.2 moles) of methacrylic acid, 20 g of p-toluenesulfonic acid, 2.16 g of hydroquinone and 200 g of n-hexane. The temperature was raised while introducing air at rate of 50 ml/min, and the reaction solution was refluxed with heating while removing the water formed (the reaction temperature: 70° to 75° C.). From about 1 hour after the beginning of reaction, adherence of a polymer to the inner wall of the flask and coloration of the reaction solution became remarkable. But the rection was still continued, and 10 hours after the beginning of reaction, heating was stopped because the formation of reaction water ceased substantially. At that time, a considerable amount of a polymer had adhered to the inner wall of the flask but no polymer was observed in the hexane solution. Therefore, only the hexane solution was taken out and washed with a 5% aqueous sodium hydroxide solution to remove the p-toluenesulfonic acid, the surplus methacrylic acid and hydroquinone, etc. The residue was further washed with water, after which 0.1 g of hydroquinone monomethyl ether was added and the hexane was removed by distillation. The liquid thus obtained contained no polymer but had a brown color (hue: 1000 hazen unit). It had a purity of 97.2% (by area) as measured by gas-chromatographic analysis. The amount of the liquid was 80 g and the yield was 37%. When 10 g of that methacrylate ester of the adduct of allyl alcohol with ethylene oxide was placed in a 18 mm$\phi$ test tube and heated at 110° C., it was solidified by polymerization after 30 minutes.

EXAMPLE 7

In the same apparatus as in Example 1 were placed 200.4 g (0.3 moles) of an adduct of bisphenol A with ethylene oxide

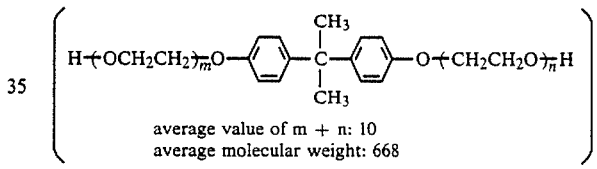

average value of m + n: 10
average molecular weight: 668

(obtained by addition-polymerization of ethylene oxide to bisphenol A) and 0.3 g of lithium hydride, and gently stirred at 40° C. for 1 hour. Thereto were added 240 g (2.4 moles) of methyl methacrylate and 0.06 g of hydroquinone monomethyl ether, and the reaction was carried out (the reaction temperature 100° to 115° C.) in the same manner as in Example 1 while introducing air at a rate of 50 ml/min. The raction was followed by analysis with a high-performance liquid chromatography.

Filtration and removal of a portion of the methyl methacrylate by distillation were conducted in the same manner as in Example 2 to obtain 228 g of light-yellow and transparent liquid (hue: 100 hazen unit). The purity of the thus obtained dimethacrylate ester of the adduct of bisphenol A with ethylene oxide was 95.5%, and the balance was monester, etc. No polymer was detected. In a 18 mm$\phi$ test tube was placed 10 g of the methacrylate ester, and heated at 110° C. for 2 hours, but no change occured.

Comparative Example 7

Into the same apparatus as in Example 1 were charged 200.4 g of an adduct of bisphenol A with ethylene oxide, 4.0 g of titanium tetraisopropoxide, 240 g of methyl methacrylate and 0.06 g of hydroquinone mononmethyl ether, and the reaction was carried out in the same manner as in Example 1 while introducing air at a rate of 50 ml/min. A polymer was formed 2 hours after the beginning of reaction, and when heating was still continued, the reaction mixture increased in viscosity to become unable to be stirred, after about 2 hours.

EXAMPLE 8

Into the same apparatus as in Example 1 was charged 116.4 g (0.6 moles) of tetraethylene glycol (H+OCH$_2$CH$_2$)$_4$OH, molecular weight 194), followed by adding thereto 1.0 g of granular sodium hydroxide, and they were gently stirred at 80° C. for 20 minutes. The resulting mixture was cooled to 40° C., after which 400 g (4.0 moles) of methyl methacrylate and 0.10 g of hydroquinone monomethyl ether were charged into the apparatus, and the reaction was carried out in the same manner as in Example 1 while blowing air through the reaction mixture at a rate of 50 ml/min. Every 30 minutes after the beginning of reaction, another 0.5 g each of a 28% methanolic solution of sodium methoxide was added. After completion of the reaction, the reaction mixture was treated in the same manner as in Example 3 to obtained 185 g of light-yellow and transparent liquid (hue: 120 hazen unit, purity: 96.5%) containing no polymer. In a 18 mm$\phi$ test tube was placed 10 g of the tetraethylene glycol dimethacrylate ester, and heated at 110° C. for 2 hours, but no change occured.

EXAMPLE 9

Into a 1-liter four-necked flask equipped with a stirrer, a thermometer, and air inlet tube and a rectifying column (15 trays) was charged 150 g (1 mole) of tricyclo[5.2.1.0$^{2,6}$]deca-3-en-8 or 9-ol

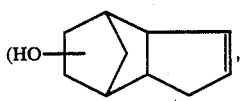

peroxide content: 48 ppm in terms of H$_2$O$_2$) followed by adding thereto 1.5 g of granular sodium hydroxide. After gentle stirring at 30° C. for 1 hour, the resulting mixture was analyzed for peroxide to detect none. Then, 350 g (3.5 moles) of methyl methacrylate and 0.11 g of hydroquinone monomethyl ether were charged into the flask, and the temperature was raised while introducing air into the reaction mixture at a rate of 50 ml/min. When the temperature of the reaction mixture reached about 100° C., an azeotropic mixture of methanol and methyl methacrylate began to be distilled out from the top of the rectifying column. Therefore, adjusted the reflux ratio to 2 and the temperature at the top of the column to 64° to 66° C., and the reaction was carried was while distilling off the methanol as an azeotrope with methyl metacylate.

One hour and 2 hours after the beginning of reaction, another 0.5 g each of granular sodium hydroxide was added. The temperature at the top of the column began to rise after about 2.5 hours of the reaction and reached to about 90° C. With the temperature rise, the reflux ratio was gradually increased finally to 10, and the reaction was continued for another 1.5 hours. The reaction mixture at 4 hours after the beginning of reaction was analyzed by a gas chromatography to find that the amount of the starting alcohol, tricyclo[5.2.1.0$^{2,6}$]deca-3-en-8 or 9-ol was 0.15% (by area) based on the amount of the product, methacrylate ester of the alcohol. At the moment the reaction was terminated. No peroxide was dtected in the reaction mixture after the termination of the reaction. The reaction mixture did not contain any polymer formed.

Subsequently, the temperature of the reaction mixture was adjusted to 100° C. and a portion of the methyl methacrylate was removed by distillation while reducing the pressure gradually. Finally the pressure was adjusted to 40 mmHg, and the concnetration was stopped at the time when the methyl methacrylate content become 0.15% as measured by gas-chromatographic analysis. The concentrate thus obtained was cooled to room temperature and filtered through filter paper (TOYO Roshi K.K.; 5B) on a Buchner funnel to obatin 210 g of light-yellow and transparent liquid (neither peroxide non polymer was detected therein). The liquid was analyzed by a gas chromatography to find that the purity (% by area) of the desired compound methacrylate ester of tricyclo[5.2.1.0$^{2,6}$]deca-3-en-8 or 9-ol was 98.6%.

EXAMPLE 10

Into the same apparatus as in Example 9 was charged 208 g (1 mole) of propylene glycol monodicyclopentenyl ether

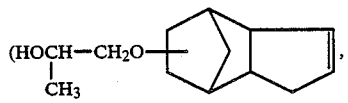

peroxide content: 63 ppm in terms of H$_2$O$_2$), followed by adding thereto 1.0 g of a 28% methanolic solution of sodium metoxide, and they were stirred at 25° C. for 30 minutes. At this time, no peroxide was detected in the alcohol. Into the apparatus were charged 350 g (3.5 moles) of methyl methacrylate and 0.11 g of hydroquinone monomethyl ether, and the reaction was carried out in the same manner as in Example 9. At 1 hour and 2 hours of the reaction, another 1.0 g each of a 28% methanolic solution of sodium methoxide was added. After completion of the reaction, no peroxide was detected in the reaction mixture. Furthermore, no polymer formed was contained therein. In the same manner as in Example 1, a portion of the methyl methacrylate was distilled off, followed by filtration, whereby 260 g of light-yellow and transparent liquid was obtained (neither peroxide nor polymer was detected in the liquid). As a result of gas-chromatographic analysis of the liquid, the purity of the methacrylate ester of propylene glycol monodicyclopentenyl ether was found to be 98.7%.

EXAMPLE 11

Into the same apparatus as in Example 9 was charged 165 g (1.5 moles) of bicyclo[2.2.1]hept -2-en-5-ol

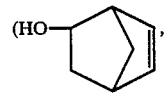

peroxide content: 18 ppm in terms of H$_2$O$_2$), followed by adding thereto 0.3 g of lithium hydride, and they were gently stirred at 50° C. for 1 hour. At the time, no peroxide was detected in the alcohol. Into the apparatus were charged 450 g (4.5 moles) of methyl methacrylate and 0.2 g of hydroquinone monomethyl ether, and the reaction was carried out in the same manner as in Example 1. In the course of the reaction, no lithium hydride was added. After completion of the reaction, no peroxide was detected in the reaction mixture. Furthermore, no polymer formed was contained therein. In the same manner as in Example 1, a portion of the methyl methacrylate was distilled off, followed by filtration, whereby 258 g of light-yellow and transparent liquid was obtained (neither peroxide nor polymer was detected in the liquid). The result of gas-chromatographic analysis indicated that the purity of the methacrylate ester of bicyclo[2.2.1]hept-2-en-5-ol was 98.8%.

EXAMPLE 12

Into the same apparatus as in Example 9 were charged 194 g (1 mole) of ethylene glycol monodicyclopentenyl ether

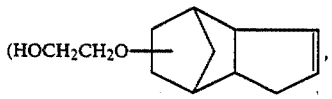

peroxide content: 35 ppm in terms of $H_2O_2$) and then 0.4 g of lithium hydroxide (anhydrous), and they were stirred at 30° C. for 2 hours. At that time, no peroxide was detected in the alocohol. In the apparatus were charged 350 (3.5 moles) of methyl methacrylate and 0.08 g of phenothiazine, and the reaction was carried out in the same as in Example 9. At 1 hour of the reaction, another 0.4 g of lithium hydroxide was added. No peroxide was detected in the reaction mixture after completion of the reaction. Furthermore, no polymer formed was contained therein. In the same manner as in Example 1, a portion of the methyl methacrylate was distilled off, followed by distillation, whereby 255 g of light-yeollow and transparent liquid was obtained (neither peroxide nor polymer was detected in the liquid). The result of gas-chromatographic analysis indicated that the purity of this methacrylate ester of ethylene glycol monodicyclopentenyl ether was 98.8%.

EXAMPLE 13

Into the same apparatus as in Example 9 was charged 152 g (1 mole) of tricyclo[$5.2.1.0^{2,6}$]decan-8-ol

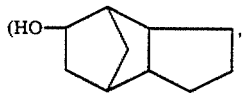

peroxide content: 15 ppm in terms of $H_2O_2$), followed by adding thereto 1.0 g of potassium hydroxide, and they were stirred at 90° C. for 30 minutes. Into the apparatus were charged 350 g (3.5 moles) of methyl methacrylate and 0.02 g of hydroquinone monomethyl ether, and the reaction was carried out in the same manner as in Example 9. Thirty minutes after the beginning of reaction, another 0.5 of lithium hydroxide was added. No peroxide was detected in the reaction mixture after completion of the reaction. Furthermore, no polymer formed was contained therein. In the same manner as in Example 1, a portion of the methyl methacrylate was distilled off, followed by filtration, whereby 212 g of light-yellow and transparent liquid was obtained (neither peroxide nor polymer was detected in the liquid). The result of gas-chromatographic analysis indicated that the purity of this methacrylate ester of tricyclo[$5.2.1.0^{2,6}$]-decan-8-ol was 98.5%.

EXAMPLE 14

Into the same apparatus as in Example 9 were charged 194 g (1 mole) of ethylene glycol monodicyclopentenyl ether

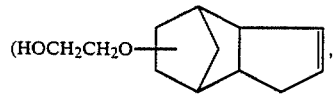

peroxide content: 35 ppm in terms of $H_2O_2$) and then 0.5 g of a 28% methanolic solution of sodium methoxide, and they were stirred at 25° C. for 20 minutes (no peroxide was detected). Into the apparatus were charged 350 g (3.5 moles) of methyl methacrylate and 0.08 g of phenothiazine, and the reaction was carried out in the same manner as in Example 9. At 30 minutes, 1 hour and 2 hours of the reaction, another 0.2 g each of a 28% methanolic solution of sodium methoxide was added. No peroxide was detected in the reaction mixture after completion of the reaction. Furthermore, no polymer formed was contained therein. The reactrion mixture was washed with two 100 g portions of a 10% aqueous sodium chloride solution, after which the methyl methacrylate was distilled off and the residue was filtered to obtain 253 g of light-yellow and transparent liquid (neither peroxide nor polymer was detected in the liquid). The result of gas-chromatographic analysis indicated that the purity of the methacrylate ester of ethylene glycol monodicyclopentenyl ether was 98.7%.

Comparative Example 8

Into the same apparatus as in Example 9 were charged 150 g (1 mole) of tricyclo[$5.2.1.0^{2,6}$]deca-3-en-8 or 9-ol

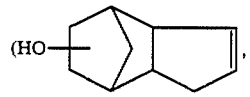

peroxide content: 48 ppm in terms of $H_2O_2$), 3.0 g of titanium tetraisopropoxide, 0.11 g of hydroquinone monomethyl ether and 350 g (3.5 moles) of methyl methacrylate, and the reaction was carried out while introducing air at a rate of 50 ml/min. Ten minutes after the beginning of the reaction, a polymer has been formed (when a small amount of the reaction solution was collected, freed from titanium tetraisopropoxide, and subjected to the methanol solubility test, the polymer was deposited, resulting in white turbidity). The concnetration of peroxide in the reaction solution at that time was about 300 ppm (in terms of $H_2O_2$). When the reaction was still continued, marked formation of a polymer was observed after 1 hour and the reaction solution increased in viscosity to become unable to be stirred.

Comparative Example 9

Into the same apparatus as in Example 9 were charged 194 g (1 mole) of ethylene glycol monodicyclopentenyl ether

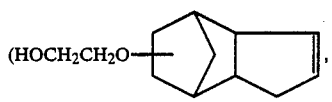

peroxide content: 35 ppm in terms of H$_2$O$_2$), 350 g (3.5 moles) of methyl methacrylate and 0.08 g of phenothiazine, and the temperature was raised while introducing air at a rate of 50 ml/min. After 15 minutes, the temperature of the solution in the apparatus became 100° C. At that time, 0.4 g of lithium hydroxide was added, and the reaction was carried out. At 1 hour of the reaction, another 0.4 g of lithium hydroxide was added. Formation of a polymer was detected at the beginning of reaction. Thirty minutes after the beginning of reaction, it was observed that the reaction mixture had become turbid owing to the polymer. However, the reaction mixture did not become unable to be stirred owing to an increase of its viscosity, and underwent the reaction for 4 hours. In the same manner as in Example 1, a portion of the methyl methacrylate was removed by distillation from the reaction mixture after completion of the reaction and the residue was filtered. The liquid thus obtained had a deep-red color and was not usuable as it was as a product. When the liquid and methanol were mixed in ratio of 1:1, a white precipitate of polymer was formed. HLC analysis indicated that the polymer content of the liquid was about 4%.

Comparative Example 10

Into the same apparatus as in Example 9 were charged 194 g (1 mole) of ethylene glycol monodicyclopentenyl ether

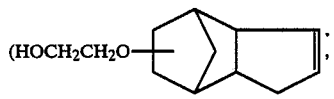

no peroxide was detected) which had been washed with a 20% aqueous sodium hydroxide solution to decompose peroxide, and then dried over Glauber's salt, 350 g of methyl methacrylate, 0.08 g of phenothiazine and 3.0 g of titanium tetraisopropoxide. The reaction was carried out in the same manner as in Example 1. Formation of a polymer was detected 20 minutes after the beginning of reaction. The concentration of peroxide in the reaction mixture at that time was about 250 ppm (in terms of H$_2$O$_2$). When heating was still continued, marked formation of a polymer was observed after 30 minutes and the reaction mixture increased in viscosity to become unable to be stirred.

Comparative Example 11

Into the same apparatus as in Example 9 were charged 152 g (1 mole) of tricyclo[5.2.1.0$^{2,6}$]decan-8-ol

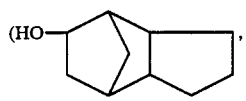

peroxide content: 15 ppm in terms of H$_2$O$_2$), 350 g (3.5 moles) of methyl methacrylate, 0.02 g of hydroquinone monomethyl ether and 3.0 g of titanium tetraisopropoxide, and the reaction was carried out in the same manner as in Example 1. Formation of a polymer was detected 1.5 hours after the beginning of reaction. At that time, the peroxide concentration in the reaction mixture was about 300 ppm (in terms of H$_2$O$_2$). When heating was still continued, marked formation of a polymer was observed after 1 hour and the reaction mixture increased greatly in viscosity.

Comparative Example 12

Into the same apparatus as in Example 9 were charged 194 g (1 mole) of ethylene glycol monodicyclopentenyl ether

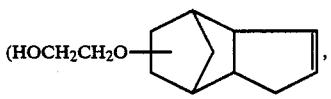

peroxide content: 35 ppm in terms of H$_2$O$_2$), and 5 g of p-toluenesulfonic acid. The temperature was raised to 60° C. with stirring and kept there for 10 minutes. Then, 350 g of methyl methacrylate and 0.13 g of 4-methoxyphenol were charged into the apparatus, and thereafter the reaction was carried out in the same manner as in Example 1. One hour after the beginning of raction, the reaction solution was colored dark-brown so seriously that when it was placed in a 18 mm diameter test tube, a substance on one side of the test tube could not be seen through the test tube from the other side. At that time the conversion was 25%. In addition, oligomer by-products having a molecular weight of about 700 to 1000 (which were presumed to be oligomers formed by ionic polymerization of dicyclopentadiene) had been formed in an amount of about 2%.

We claim:

1. A method for producing a methacrylate ester of an alcohol having at least one ether linkage and/or at least one alicyclic ring, which comprises treating said alcohol with alkaline substance which is lithium hydroxide or lithium alkoxide, and then reacting the same with methyl methacrylate in the presence of said alkaline substance.

2. A method for producing a methacrylate ester of an alcohol having at least one ether linkage and/or at least one alicyclic ring, which comprises treating said alcohol with alkaline substnace which is lithium hydroxide, and then reacting the same with methyl methacrylate in the presence of said alkaline substance.

3. A method for producing a methacrylate ester of an alcohol having at least one ether linkage and/or at least one alicyclic ring, which comprises treating said alcohol with alkaline substance which is lithium hydroxide or lithium alkoxide, and then reacting the same with methyl methacrylate in the presence of said alkaline substance, wherein said alcohol is stirred together with said alkaline substance and then methyl methacrylate is added to react with the alcohol.

4. A method for producing a methacryalte ester of an alcohol having at least one ether linkage and/or at least one alicyclic ring, which comprises treating said alcohol with alkaline substance which is lithium hydroxide, and then reacting the same with methyl methacrylate in the presence of said alkaline substance, wherein said alcohol is stirred together with said alkaline substance and then methyl methacrylate is added to react with the alcohol.

5. A method for producing a methacrylate ester of an alcohol having at least one ether linkage and/or at least one alicyclic ring, which comprises treating said alcohol with alkaline substance which is lithium hydroxide or lithium alkoxide, and then after no peroxide was detected in said alcohol, reacting the same with methyl methacrylate in the presence of said alkaline substance.

6. A method for producing a methacrylate ester of an alcohol haivng at least one ether linkage and/or at least one alicyclic ring, which comprises treating said alcohol with alkaline substance which is lithium hydroxide, and then after no peroxide was detected in said alcohol, reacting the same with methyl methacrylate in the presence of said alkaline substance.

7. A method for producing a methacrylate ester of an alcohol having at least one ether linkage and/or at least one alicyclic ring, which comprises treating said alcohol with alkaline substance which is lithium hydroxide or lithium alkoxide, and then reacting the same with methyl methacrylate in the presence of said alkaline substance, wherein the alcohol is stirred together with said alkaline substance, and then after no peroxide was detected in said alcohol, methyl methacrylate is added to react with the alcohol.

8. A method for producing a methacryalte ester of an alcohol having at least one ether linkage and/or at least one alicyclic ring, which comprises treating said alcohol with alkaline substance which is lithium hydroxide, and then reacting the same with methyl methacrylate in the presence of said alkaline substance, wherein the alcohol is stirred together with said alkaline substance, and then after no peroxide was detected in said alcohols, methyl metacrylate is added to react with the alcohol.

9. A method according to claim 1, 2, 3, 4, 5, 6, 7 or 8, wherein the ether linkage containing alcohol is a compound represented by the following general formula (I), (II) or (III):

$$HO-(R^1O)_kH \qquad (I)$$

(wherein $R^1$ is an alkylene group, and k is an integer), $$R^2-O-(R^1O)_lH \qquad (II)$$

(wherein $R^1$ is an alkylene group, $R^2$ is a hydrocarbon group, and l is an integer), or $$H-(OR^1)_mO-R^3-O-(R^1O)_nH \qquad (III)$$

(wherein $R^1$ is an alkylene group, $R^3$ is a divalent group, and each of m and n is an integer).

10. A method according to claim 1, 2, 3, 4, 5, 6, 7 or 8, wherein the ether linkage containing alcohol is one which contains at least on double bond.

11. A method accoridng to claim 1, 2, 3, 4, 5, 6, 7 or 8, wherein the alicyclic alcohol is one which contains at least one alicyclic group having at least one tertiary carbon atom in the ring.

12. A method according to claim 1, 2, 3, 4, 5, 6, 7 or 8, wherein the alicyclic alcohol is one which contains at least one alicyclic group having at least one double bond in the ring.

13. A method according to claim 1, 2, 3, 4, 5, 6, 7 or 8, wherein the alicyclic alcohol is one which contains at least one alicyclic group having at least one tertiary carbon atom and at least one double bond in the ring.

14. A method for producing a methacrylate ester of an alcohol haivng at leat one ether linkage, at least alicyclic ring and at least one double bond, which comprises treating said alcohol with alkaline substance which is lithium hydroxide or lithium alkoxide, and then reacting the same with methyl metacrylate in the presence of said alkaline substance.

15. A method for producing a metacrylate ester of an alcohol having at least one ether linkage, at least alicyclic ring and at least one double bond, which comprises treating said alcohol with alkaline substance which is lithium hydroxide, and then reacting the same with methyl methacrylate in the presence of said alkaline substance.

16. A method for producing a methacrylate ester of an alcohol having at least one ether linkage, at least alicyclic ring and at least one double bond, which comprises treating said alcohol with alkaline substance which is lithium hydroxide or lithium alkoxide, and then reacting the same with methyl methacrylate in the presence of said alkaline substance, wherein the alcohol is stirred together with said alkaline substance and then methyl methacrylate is added to react with the alcohol.

17. A method for producing a methacrylate ester of an alcohol having at least one ether linkage, at least alicyclic ring and at least one double bond, which comprises treating said alcohol with alkaline substance which is lithium hydroxide, and then reacting the same with methyl methacrylate in the presence of said alkaline substnace, wherein the alcohol is stirred together with alkaline substance, and then methyl methacrylate is added to react with the alcohol.

18. A method for producing a methacrylate ester of an alcohol having at least one ether linkage, at least alicyclic ring and at least one double bond, which comprises treating said alcohol with alkaline substance which is lithium hydroxide or lithium alkoxide, and then after no peroxide was detected in said alcohol, reacting the same with methyl metacrylate in the presence of said alkaline substance.

19. a method for producing a methacrylate ester of an alcohol having at least one ether linkage, at least alicyclic ring and at least one double bond, which comprises treating said alcohol with alkaline substance which is lithium hydroxide and then after no peroxide was detected in said alcohol, reacting the same with methyl methacrylate in the presence of said alkaline substance.

20. A method for producing a methacrylate ester of an alcohol having at least one ether linkage, at least alicyclic ring and at least one double bond, which comprises treating said alcohol with alkaline substance which is lithium hydroxide or lithium alkoxide, and then reacting the same with methyl methacryalte in the presence of said alkaline substance, wherein the alcohol is stirred together with said alkaline substance, and then after no peroxide as detected in said alcohol, methyl methacrylate is added to react with the alcohol.

21. A method for producing a methacrylate ester of an alcohol having at least one ether linkage, at least alicyclic ring and at least one double bond, which comprises treating said alcohol with alkaline substance which is lithium hydroxide and then reacting the same with methyl methacrylate in the presence of said alkaline substance, wherein the alcohol is stirred together with said alkaline substnace, and then after no peroxide was detected in said alcohol, methyl methacrylate is added to react with the alcohol.

22. A method according to claim 14, 15, 16, 17, 18, 19, 20 or 21, wherein an alcohol having at least one ether linkage, at least one alicyclic ring and a double bond which is a compound formed by addition of ethylene oxide or propylene oxide to norbornenyl alcohol, norbornenylmethyl alcohols, tricyclo[5.2.1.0$^{2,6}$]deca-3-en-8-ol or tricyclo[5.2.1.0$^{2,6}$]deca-3-en-9-ol, or a compound formed by addition of ethylene glycol or propylene glycol to tricyclo[5.2.1.0$^{2,6}$]deca-3,8-diene followed by addition-polymerization to the resulting adduct of ethylene oxide or propylene oxide.

23. A method according to claim 14, 15, 16, 17, 18, 19, 20 or 21, wherein an alcohol having at least one ether linkage, at least one alicyclic ring and at least one double bond which is ethylene glycol monodicyclopentenyl ether, propylene glycol monodicyclopentenyl ether, neopentyl glycol monodicyclopentenyl ether or 1,6-hexane-diol monodicyclopentenyl ether.

24. A method for producing a methacrylate ester represented by the following general formula (IV):

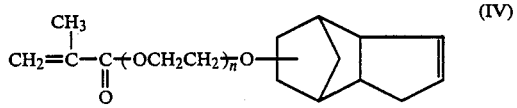
(IV)

(wherein n is an integer)
which comprises treating the alcohol represented by the following general formula (V):

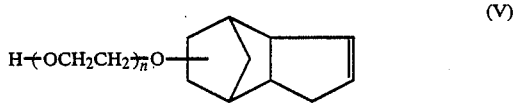
(V)

(wherein n is an integer)
with lithium hydroxide, and then after no peroxide was detected in said alcohol, reacting the same with methyl methacrylate in the presence of lithium hydroxide.

25. A method according to claim 24, wherein the interger of n is from 1 to 6.

26. A method for producing a methacrylate ester represented by the following general formula (VI):

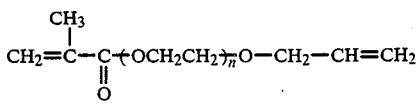
(VI)

(wherein n is an integer)
which comprises treating the alcohol represented by the following general formula (VIII):

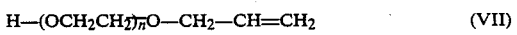
(VII)

(wherein n is an integer)
with lithium hydroxide, and then after no peroxide was detected in said alcohol, reacting the same with methyl methacrylate in the presence of lithium hydroxide.

27. A method according to claim 26, wherein the integer of n is 2.

28. A method according to claim 1, 2, 3, 4, 5, 6, 7, 8, 18, 19, 20, 21, 24 or 26, wherein the reaction is carried out in the presence of hydroquinone monomethyl ether or phenothiazine in amount of 15 to 10000 ppm relative to the starting said alcohol.

29. A method according to claim 1, 2, 3, 4, 5, 6, 7, 8, 18, 19, 20, 21, 24 or 26, wherein the reaction is carried out in the presence of hydroquinone monomethyl ether or phenothiazine in amount of 15 to 10000 ppm relative to the starting said alcohol and while blowing molecular oxygen through the reaction system.

30. A method according to claim 1, 2, 3, 4, 5, 6, 7, 8, 18, 19, 20, 21, 24 or 25, wherein the alkaline substance is present in an amouont of 0.01 to 10.0% by weight based on the weight of the starting alcohol.

31. A method according to claim 1, 2, 3, 4, 5, 6, 7, 8, 18, 19, 20, 21, 24 or 26, wherein the alkaline substance is present in an amount of 0.01 to 10.0% by weight based on the weight of the starting alcohol and the reaction is carried out in the presence of hydroquinone monomethyl ether or phenothiazine in amount of 15 to 10000 ppm relative to the starting said alcohol and while blowing molecular oxygen through the reaction system.

32. A method according to claim 1, 2, 3, 4, 5, 6, 7, 8, 18, 19, 20, 21, 24 or 26, wherein lithium alkoxide is one which is lithium methoxide, lithium ethoxide, lithium propoxide or lithium butoxide.

* * * * *

UNITED STATES PATENT AND TRADEMARK OFFICE
CERTIFICATE OF CORRECTION

PATENT NO.   : 4,916,255
DATED        : April 10, 1990
INVENTOR(S)  : KOBAYASHI, et al It is certified that error appears in the above-identified patent and that said Letters Patent is hereby corrected as shown below:

On the Title Page, left-hand column

Item [73] Assignee: "Hitachi, Ltd., Tokyo, Japan"

should read

--[73] Assignee:  Hitachi Chemical Company, Ltd., Tokyo, Japan--

Signed and Sealed this

Twenty-ninth Day of December, 1992

Attest:

DOUGLAS B. COMER

Attesting Officer

Acting Commissioner of Patents and Trademarks